United States Patent [19]

Berendes et al.

[11] 4,384,145
[45] May 17, 1983

[54] PROCESS FOR THE PREPARATION OF PINACOLONE

[75] Inventors: Otto Berendes, Dormagen; Peter Siegle, Cologne, both of Fed. Rep. of Germany

[73] Assignee: Bayer Aktiengesellschaft, Leverkusen, Fed. Rep. of Germany

[21] Appl. No.: 276,841

[22] Filed: Jun. 24, 1981

[30] Foreign Application Priority Data

Jul. 8, 1980 [DE] Fed. Rep. of Germany ....... 3025777

[51] Int. Cl.³ .............................................. C07C 1/00
[52] U.S. Cl. .................................................. 568/391
[58] Field of Search ........................ 568/391, 347, 315

[56] References Cited

U.S. PATENT DOCUMENTS 2,430,436 11/1947 Tindall ................................. 568/391
2,957,889 10/1960 Hoaglin et al. ...................... 568/391
4,224,252 9/1980 Kyo et al. ............................ 568/391

FOREIGN PATENT DOCUMENTS 2918521 11/1979 Fed. Rep. of Germany ...... 568/391
2364876 4/1978 France ................................ 568/391

OTHER PUBLICATIONS

Tanaka et al., Chem. Abst., vol. 91, #192827y (1979).

McOmie, "Protective Groups in Organic Chem.", pp. 96–97, Plenum Press (1973).

*Primary Examiner*—James H. Reamer
*Attorney, Agent, or Firm*—Felfe & Lynch

[57] ABSTRACT

This invention relates to a new process for the preparation of pinacolone (2.2-dimethyl-3-oxobutane) of the formula $$(CH_3)_3C-CO-CH_3 \qquad (I),$$

which process comprises reacting a 2-alkoxy-2-methylbutane of the formula

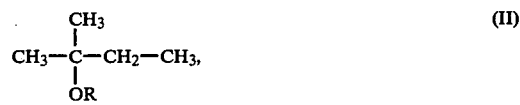

wherein
R is alkyl of from 1 to 4 carbon atoms
with formaldehyde at a temperature of 40° to 100° C., in an aqueous medium and in the presence of a strong inorganic acid.

Pinacolone (I) can be used as a solvent, and also as an intermediate product in organic synthesis, for example for the production of known herbicides.

13 Claims, No Drawings

PROCESS FOR THE PREPARATION OF PINACOLONE

This invention relates to a novel process for the preparation of pinacolone (2,2-dimethyl-3-oxobutane).

It is known that pinacolone is obtained when 2-methyl-but-2-ene (or 2-methyl-but-1-ene) is reacted with formaldehyde under certain conditions, in an aqueous medium and in the presence of a strong inorganic acid (at least 15% by weight of acid (see German Patent Specification 2,461,503). A modification of this process has also been disclosed, which is characterised in that the reaction is carried out with the addition of a salt, which is at least partly soluble in the reaction system, of a strong inorganic acid; by this measure, it is said to be possible to reduce the concentration and amount of acid which are otherwise necessary (see DE-OS (German Published Specification) 2,918,521).

In the case of a large-scale industrial procedure, the 2-methyl-butene required as the starting material for the two processes mentioned must be isolated from a C$_5$-gasoline fraction by addition of an alcohol (for example methanol), whereupon a t-amyl ether (for example t-amyl methyl ether) is formed. In a second reaction step, the tertiary ether must then be converted back into 2-methyl-butene, the alcohol being split off again.

The present invention now provides a process for the preparation of pinacolone, of the formula $$(CH_3)_3C-CO-CH_3 \qquad (I)$$

in which a 2-alkoxy-2-methylbutane of the general formula

wherein
R represents a C$_{1-4}$-alkyl radical,
is reacted with formaldehyde at a temperature between 40° and 100° C. in an aqueous medium and in the presence of a strong inorganic acid.

Compared with the prior art process described above, one reaction step is saved in that the tertiary ethers (II), that is to say the alcohol/2-methylbutene addition products, can, according to the invention, be employed directly for the pinacolonesynthesis.

It is surprising that pinacolone can be formed in good yields and in good purity in a smooth reaction from the 2-alkoxy-2-methyl-butanes. In contrast, as our own experiments have shown, only very small amounts of the corresponding position isomer, that is to say, 3-alkoxy-2-methylbutanes, can be converted into pinacolone, even under more severe conditions.

If 2-methoxy-2-methylbutane is used, the course of the reaction can be represented by the following equation:

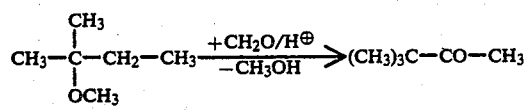

The 2-alkoxy-2-methylbutanes (II) which can be used according to the invention are known. As already stated, they can be prepared by adding the corresponding alcohols onto 2-methyl-but-2-ene or 2-methyl-but-1-ene, or onto mixtures of the two isomers, and on a large industrial scale they can be prepared by adding alcohol onto C$_5$-gasoline fractions which, in addition to other hydrocarbons, also contain the pentenes mentioned.

Examples which may be mentioned are 2-methoxy-2-methyl-butane (t-amyl methyl ether), 2-ethoxy-2-methyl-butane (t-amyl ethyl ether) and 2-propoxy-2-methylbutane (t-amyl propyl ether).

The formaldehyde required for the reaction according to the invention can be used in any of the commercially available forms and concentrations, for example as an aqueous 5–70% strength, preferably 20–60% strength, solution; however, it is also possible to employ paraformaldehyde.

The reaction is in general carried out at a temperature between 40° and 100° C., preferably between 50° and 90° C.

In carrying out the process according to the invention, 1 to 1.5 moles, preferably 1 to 1.2 moles, of formaldehyde are employed per mole of 2-alkoxy-2-methylbutane (II).

Strong inorganic acids which can be employed are, as preferences, hydrochloric acid, hydrobromic acid and sulphuric acid. The amount of inorganic acid required for the reaction according to the invention and its concentration in the aqueous phase depend on the nature of the acid. If hydrochloric acid or hydrobromic acid is used, the concentration should be 10–40%, preferably 25–40%. If sulphuric acid is used, the concentration should preferably be 20–60%, but likewise at least 10%.

The reactants tertiary ether (II) and formaldehyde can be added to the acid simultaneously or successively. It has proved particularly expedient to introduce initially the aqueous acid solution and to add the tertiary ether (II) at room temperature and then slowly to add the formaldehyde dropwise, in general in the form of an aqueous formalin solution, at elevated temperature. A subsequent after-reaction time, likewise at elevated temperature, of several hours (0.5–10 hours) before the batch is worked up is advisable.

It is also essential for the reaction according to the invention that intensive thorough, mixing of the reaction mixture is ensured during the reaction and the after-reaction. This can be achieved by using suitable stirrer speeds, and in some cases also by adding small amounts of an emulsifier to the reaction mixture.

When the reaction has ended, the reaction mixture is cooled, and rendered neutral, generally with sodium hydroxide solution; the two phases are separated. The organic phase contains the pinacolone, which is most appropriately isolated by distillation and purified.

When the reaction is carried out at relatively low temperatures and low concentrations of acid, the alcohol liberated during the reaction can be recovered from the aqueous phase, after neutralizing the batch. At elevated temperatures and higher hydrochloric acid and hydrobromic acid concentrations, the alcohol liberated is reacted to give the corresponding alkyl chloride or alkyl bromide; this compound is present in the organic phase during working up and can be separated off from the pinacolone by distillation.

Pinacolone can be used as a solvent, and also as an intermediate product in organic synthesis, for example for the preparation of known herbicidal active compounds. The synthesis of the particularly herbicidally active compound 4-amino-6-tert.-butyl-3-methylthio-1,2,4-triazin-5(4H)-one starting from pinacolone may be mentioned as an example (see DE-OS (German Published Specification) 2,648,300; German Patent Specification 2,461,503; and German Patent Specification 1,795,784).

PREPARATIVE EXAMPLES

Example 1

255 g (2.5 mol) of 2-methoxy-2-methylbutane were added to 600 ml of 38% strength hydrochloric acid at room temperature in the course of 30 minutes, while stirring. 250 g of 30% strength aqueous formalin solution (2.5 mol of formaldehyde) were then added dropwise at 70° C. in the course of 2 hours. When the addition had ended, the reaction mixture was allowed to after-react for a further 2 hours at 80° C. and was then cooled and rendered neutral with sodium hydroxide solution; the organic phase was separated off, dried and distilled.

Yield: 165 g (66% of theory) of pure pinacolone, boiling point: 106°-107° C.

70 g (55% of theory) of methyl chloride were condensed in the cold trap downstream of the distillation condenser.

Example 2

58.5 g (0.5 mol) of 2-ethoxy-2-methylbutane were added to 120 ml of 38% strength hydrochloric acid at room temperature in the course of 10 minutes, while stirring. 52.5 g of 30% strength aqueous formalin solution (0.525 mol of formaldehyde) were then added dropwise at 70° C. The after-reaction and working up were carried out as in Example 1.

Yield: 30.5 g (61% of theory) of pure pinacolone.

Example 3

51 g (0.5 mol) of 2-methoxy-2-methylbutane were added to 120 ml of 39% strength hydrobromic acid at room temperature, while stirring. 52.5 g of 30% strength aqueous formalin solution (0.525 mol of CH$_2$O) were then added dropwise at 70° C. After a 2-hour after-reaction at 80° C., the mixture was worked up, as described in Example 1.

Yield: 21 g (42% of theory) of pure pinacolone.

Example 4

102 g (1 mol) of 2-methoxy-2-methylbutane were added to 240 ml of 30% strength sulphuric acid at room temperature. 110 g of 30% strength aqueous formalin solution (1.1 mol of CH$_2$O) were then added dropwise at 54° C. in the course of 3 hours. After a 5-hour after-reaction at 70° C., the mixture was worked up as described above.

Yield: 45 g (45% of theory) of pure pinacolone. 27.2 g (85% of theory) of methanol could be isolated from the aqueous phase.

It will be understood that the specification and examples are illustrative but not limitative of the present invention and that other embodiments within the spirit and scope of the invention will suggest themselves to those skilled in the art.

What is claimed is:

1. Process for the preparation of pinacolone of the formula $$(CH_3)_3C-CO-CH_3 \qquad (I)$$

which process comprises reacting a 2-alkoxy-2-methylbutane of the formula $$\begin{array}{c} CH_3 \\ | \\ CH_3-C-CH_2-CH_3, \\ | \\ OR \end{array} \qquad (II)$$

wherein
R is alkyl of from 1 to 4 carbon atoms
with formaldehyde at a temperature of 40° to 100° C., in an aqueous medium and in the presence of a strong inorganic acid.

2. Process as claimed in claim 1 wherein the reaction is carried out at temperatures between 50° and 90° C.

3. Process as claimed in claim 1 wherein 1 to 1.5 moles of formaldehyde are employed per mole of 2-alkoxy-2-methylbutane of formula (II).

4. Process as claimed in claim 1 wherein 1 to 1.2 moles of formaldehyde are employed per mole of 2-alkoxy-2-methylbutane of formula (II).

5. Process as claimed in claim 1 wherein hydrochloric acid is employed as the strong inorganic acid.

6. Process as claimed in claim 1 wherein hydrobromic acid is employed as the strong inorganic acid.

7. Process as claimed in claim 1 wherein sulphuric acid is employed as the strong inorganic acid.

8. Process as claimed in claim 1 wherein the formaldehyde introduced is in the form of an aqueous solution of 5-70% strength.

9. Process as claimed in claim 1 wherein the formaldehyde introduced is in the form of an aqueous solution of 20-60% strength.

10. Process as claimed in claim 1 wherein the formaldehyde is introduced in the form of paraformaldehyde.

11. Process as claimed in claim 1 wherein the acid is employed at a concentration of at least 10% by weight.

12. Process as claimed in claim 1 wherein the reaction mixture is intensively mixed.

13. Process as claimed in claim 1 wherein R is methyl.

* * * * *